(12) United States Patent
Millerd et al.

(10) Patent No.: US 7,298,497 B2
(45) Date of Patent: Nov. 20, 2007

(54) METHODS AND APPARATUS FOR SPLITTING, IMAGING, AND MEASURING WAVEFRONTS IN INTERFEROMETRY

(75) Inventors: James E. Millerd, Aliso Viego, CA (US); Neal J. Brock, Lake Forest, CA (US)

(73) Assignee: MetroLaser, Inc., Irvine, CA (US)

( * ) Notice: Subject to any disclaimer, the term of this patent is extended or adjusted under 35 U.S.C. 154(b) by 0 days.

(21) Appl. No.: 11/349,843

(22) Filed: Feb. 7, 2006

(65) Prior Publication Data

US 2006/0132795 A1 Jun. 22, 2006

Related U.S. Application Data

(60) Division of application No. 10/251,729, filed on Sep. 21, 2002, now Pat. No. 7,170,611, which is a continuation of application No. 09/906,542, filed on Jul. 16, 2001, now Pat. No. 6,552,808, which is a continuation of application No. 09/413,829, filed on Oct. 6, 1999, now Pat. No. 6,304,330.

(51) Int. Cl.
*G01B 9/02* (2006.01)

(52) U.S. Cl. ........................... 356/512; 356/521

(58) Field of Classification Search ........ 356/512–515, 356/499, 498, 488, 494, 521
See application file for complete search history.

(56) References Cited

U.S. PATENT DOCUMENTS 4,076,423 A 2/1978 Bates (Continued)

FOREIGN PATENT DOCUMENTS

DE 19652113 A1 6/1998

(Continued)

OTHER PUBLICATIONS

Smythe, R., et al., "Instantaneous Phase Measuring Interferometry," *Optical Engineering* 23:4 (Jul./Aug. 1984): 361-4.

(Continued)

*Primary Examiner*—Hwa (Andrew) Lee
(74) *Attorney, Agent, or Firm*—Norman E. Carte; MacPherson Kwok Chen & Heid LLP

(57) ABSTRACT

Apparatus for splitting, imaging, and measuring wavefronts with a reference wavefront and an object wavefront. A wavefront-combining element receives and combines into a combined wavefront an object wavefront from an object and a reference wavefront. A wavefront-splitting element splits the combined wavefront into a plurality of sub-wavefronts in such a way that each of the sub-wavefronts is substantially contiguous with at least one other sub-wavefront. The wavefront-splitting element may shift the relative phase between the reference wavefront and the object wavefront of the sub-wavefronts to yield a respective plurality of phase-shifted sub-wavefronts. The wavefront-splitting element may then interfering the reference and object wavefronts of the phase-shifted sub-wavefronts to yield a respective plurality of phase-shifted interferograms. An imaging element receives and images the phase-shifted interferograms. A computer connected to the imaging element measures various parameters of the objects based on the phase-shifted interferograms. Examples of measurements include flow parameters such as the concentrations of selected gaseous species, temperature distributions, particle and droplet distributions, density, and so on. In addition to flow parameters, the displacement (e.g., the vibration) and the profile of an object may be measured.

20 Claims, 9 Drawing Sheets

U.S. PATENT DOCUMENTS

| | | | |
|---|---|---|---|
| 4,105,289 A | 8/1978 | Hershel | |
| 4,191,477 A | 3/1980 | Schick | |
| 4,399,356 A | 8/1983 | Feinleib et al. | |
| 4,575,248 A | 3/1986 | Horwitz et al. | |
| 4,583,855 A | 4/1986 | Bareket | |
| 4,624,569 A | 11/1986 | Kwon | |
| 4,690,555 A | 9/1987 | Ellerbroek | |
| 4,696,573 A * | 9/1987 | Hutchin | 356/521 |
| 4,725,138 A | 2/1988 | Wirth et al. | |
| 4,762,989 A | 8/1988 | Motooka | |
| 4,824,243 A | 4/1989 | Wheeler et al. | |
| 4,832,489 A * | 5/1989 | Wyant et al. | 356/513 |
| 4,836,681 A | 6/1989 | Van Saders et al. | |
| 5,127,731 A | 7/1992 | DeGroot | |
| 5,189,677 A | 2/1993 | Yry | |
| 5,349,432 A | 9/1994 | Elerath | |
| 5,392,116 A | 2/1995 | Makosch | |
| 5,398,113 A | 3/1995 | de Groot | |
| 5,410,397 A | 4/1995 | Toeppen | |
| 5,555,471 A | 9/1996 | Xu et al. | |
| 5,589,938 A | 12/1996 | Deck | |
| 5,663,793 A | 9/1997 | de Groot | |
| 5,777,741 A | 7/1998 | Deck | |
| 5,835,133 A | 11/1998 | Moreton et al. | |
| 5,870,191 A | 2/1999 | Shirley et al. | |
| 5,880,838 A | 3/1999 | Marx et al. | |
| 5,880,841 A | 3/1999 | Marron et al. | |
| 5,883,717 A | 3/1999 | DeMarzio et al. | |
| 5,900,936 A | 5/1999 | Shirlet et al. | |
| 5,907,404 A | 5/1999 | Marron et al. | |
| 5,914,782 A | 6/1999 | Sugiyama | |
| 5,926,283 A | 7/1999 | Hopkins | |
| 5,933,236 A | 8/1999 | Sommargren | |
| 5,982,497 A | 11/1999 | Hopkins | |
| 5,987,189 A | 11/1999 | Schmucker et al. | |
| 5,995,223 A | 11/1999 | Power | |

FOREIGN PATENT DOCUMENTS

| | | | |
|---|---|---|---|
| WO | WO 97/41478 A | 11/1997 | |

OTHER PUBLICATIONS

Barrientos, B., et al., "Transient Deformation Measurement with ESPI Using a Diffractive Optical Element for Spatial Phase-stepping," FRINGE, Akademie Verlag (1997): 371-8.

Koliopoulos, C., "Simultaneous Phase Shift Interferometer," Proc. of SPIE vol. 1531, Advanced Optical Manufacturing and Testing II, ed. V J Doherty (Jan. 1992): 119-127.

Bareket, N., "Three-Channel Phase Detector for Pulsed Wavefront Sensing," Proc. of SPIE vol. 0551, Adaptive Optics, ed. Jacques E. Ludman (Apr. 1985): 12-16.

Kwon, O., et al., "Multichannel Grating Phase-Shift Interferometer," Proc. of SPIE vol. 0599, Optics in Engineering Measurement, ed. William F. Fagan (Dec. 1985): 273-278.

Smythe, R., et al., "Instantaneous Phase Measuring Interferometry," Proc. of SPIE vol. 0429, Precision Surface Metrology, ed. James C. Wyant (Aug. 1983): 16-21.

Hettwer, A, et al., "Single-Frame-Interferometer for testing surfaces," *Lehrstuhl fur Optik—Annual Report*, Physikalisches Institut, Friedrich-Alexamder-Universitat Erlangen Nurnberg, (1997): 22.

Kranz, J., et al., "Error Analysis for a Single-frame Phase-shifting Speckle-interferometer," Proc. of SPIE vol. 3749, Part of the 18th Congress of the International Commission for Optics (Aug. 1999): 178-79.

Hettwer, A, et al., "Three Channel Phase-shiting Inferferometer Using Polarization-optics and a Diffraction Grating," Opt. Eng. vol. 39, No. 4 (Apr. 2000): 960-66.

Kranz, J., and J. Schwider, "Single-frame Realtime Interferometer (SIFRI)", www.optik.uni-erlangen.de/mikos/Projects/SIRFI/SIFRI.htm, 1998.

\* cited by examiner

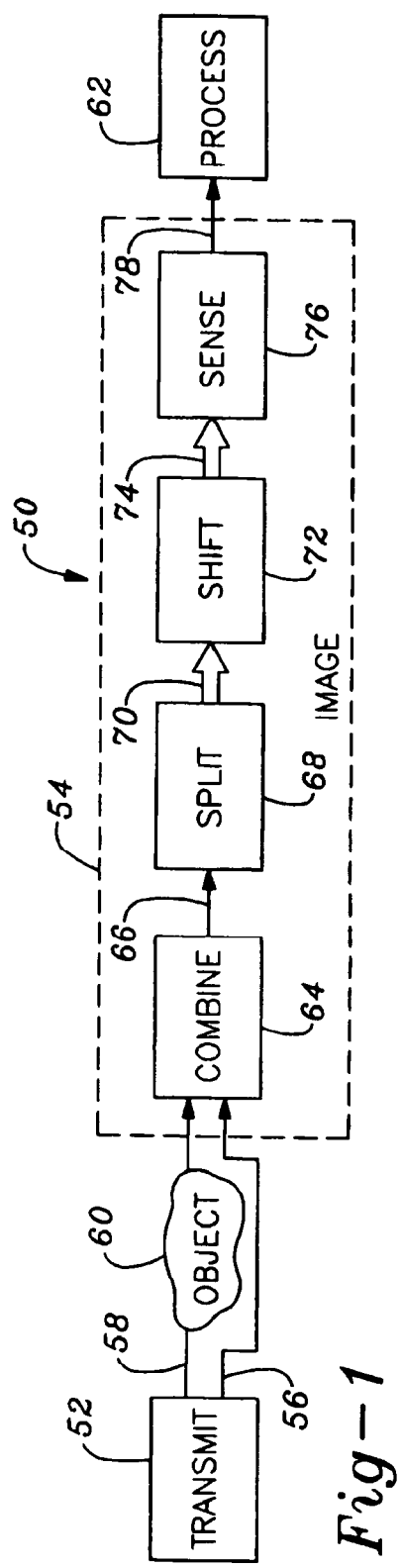
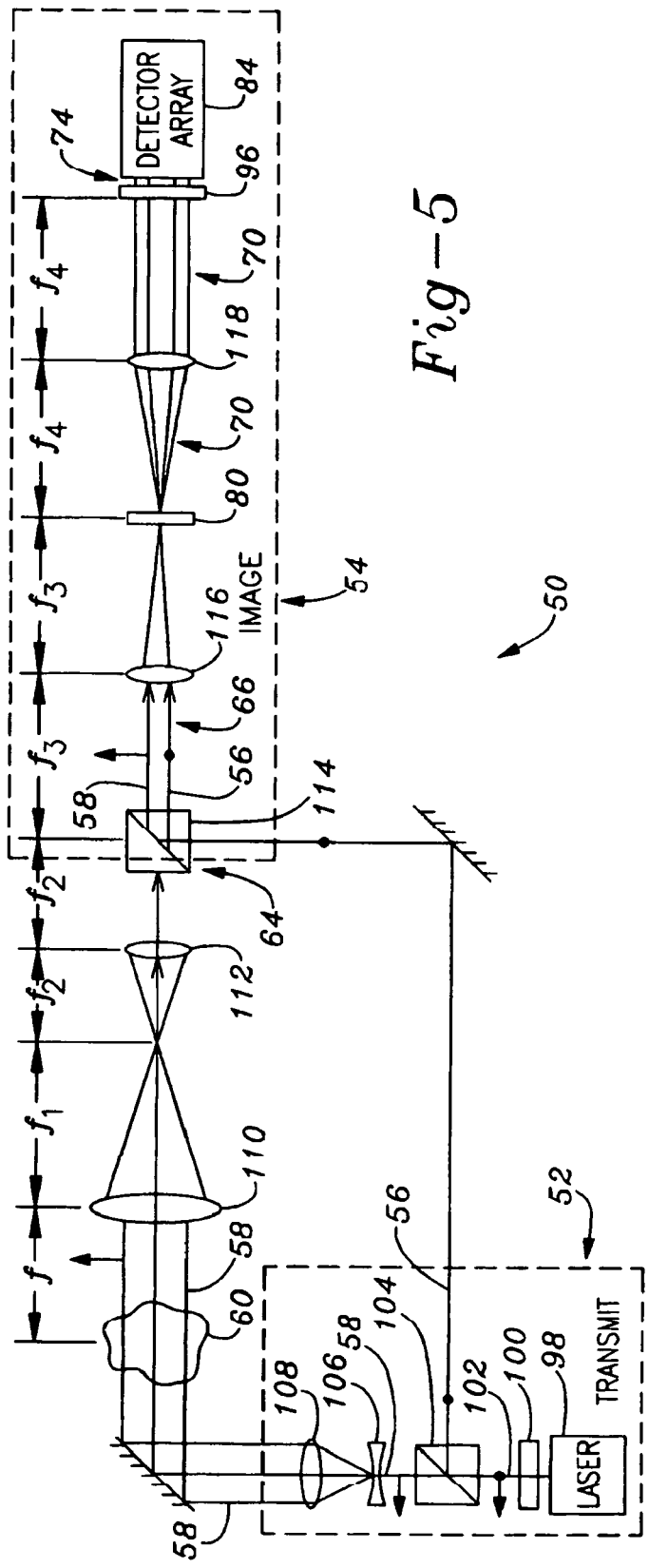

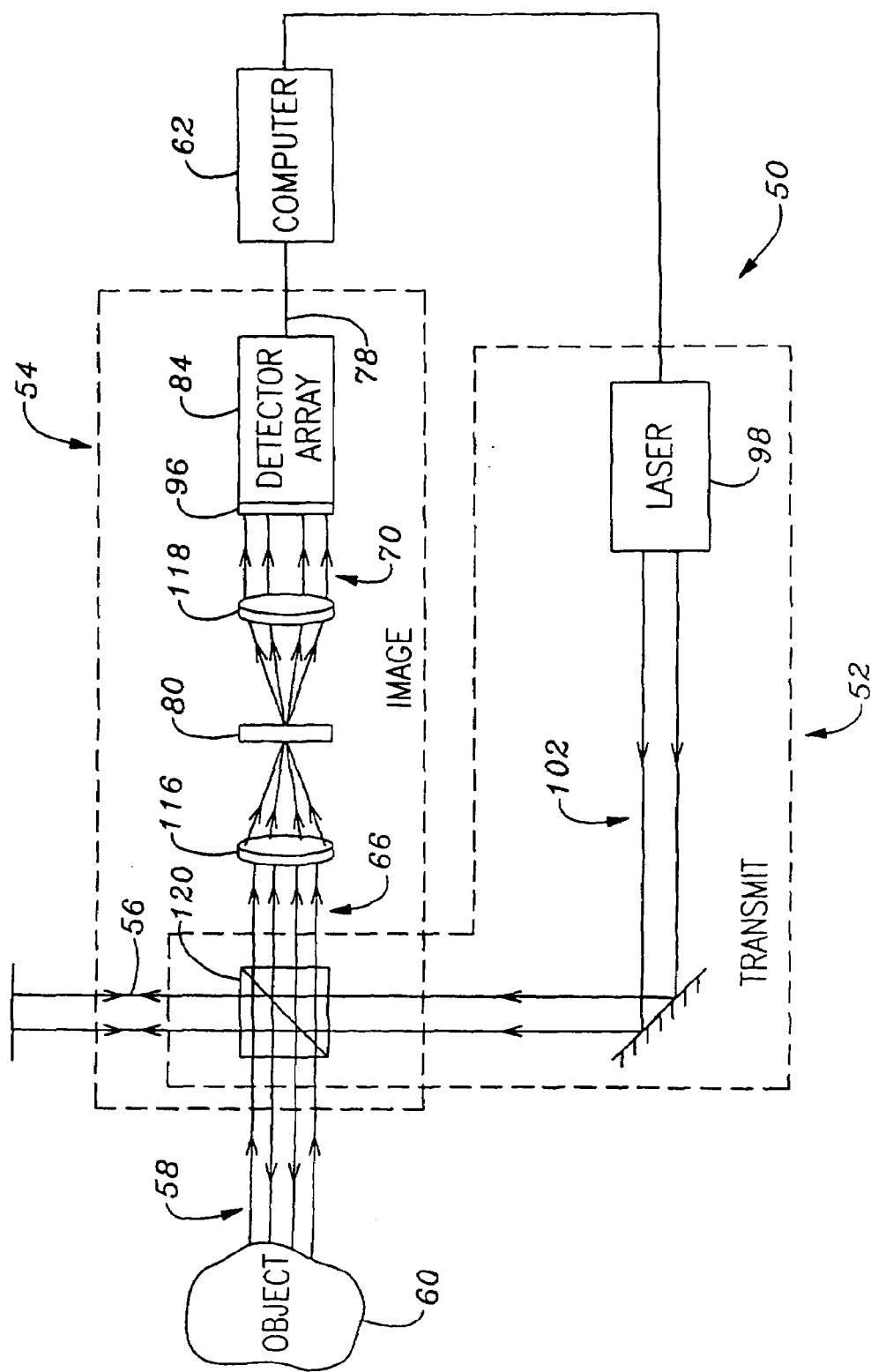

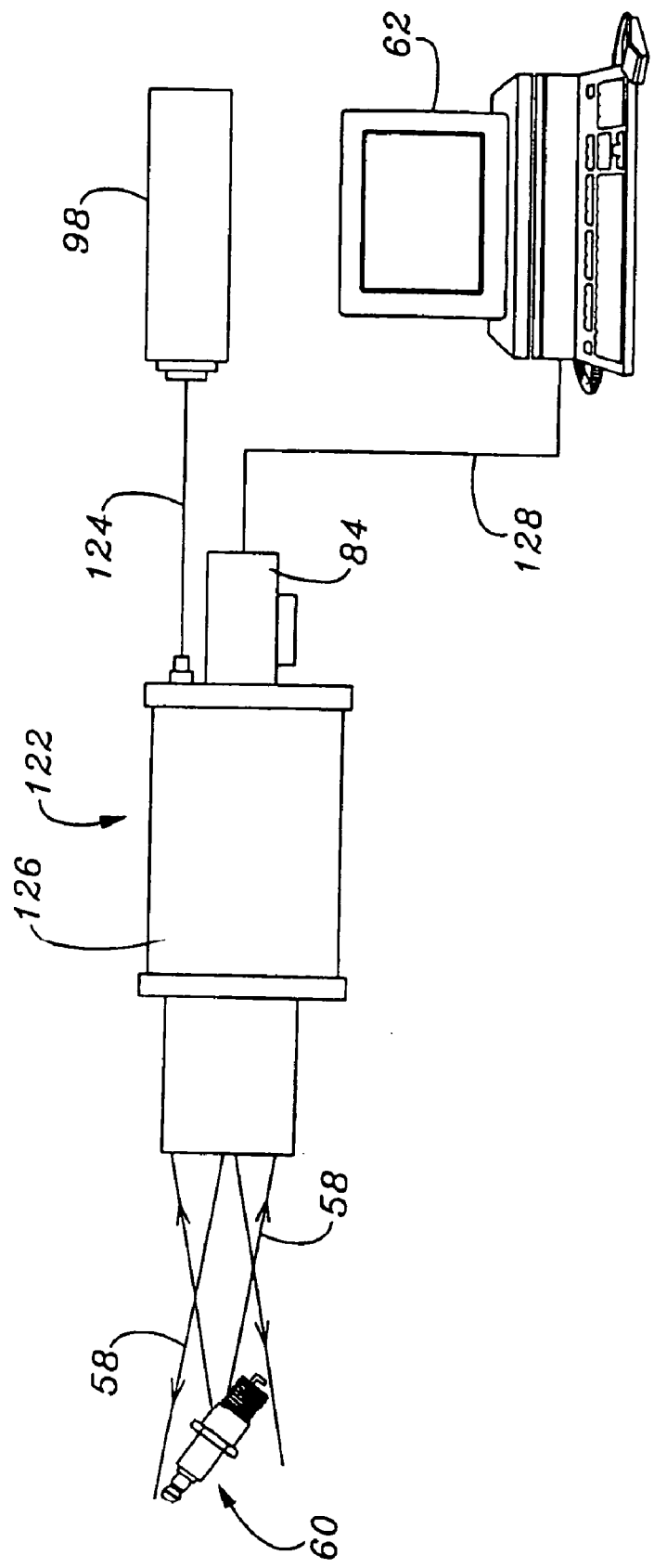

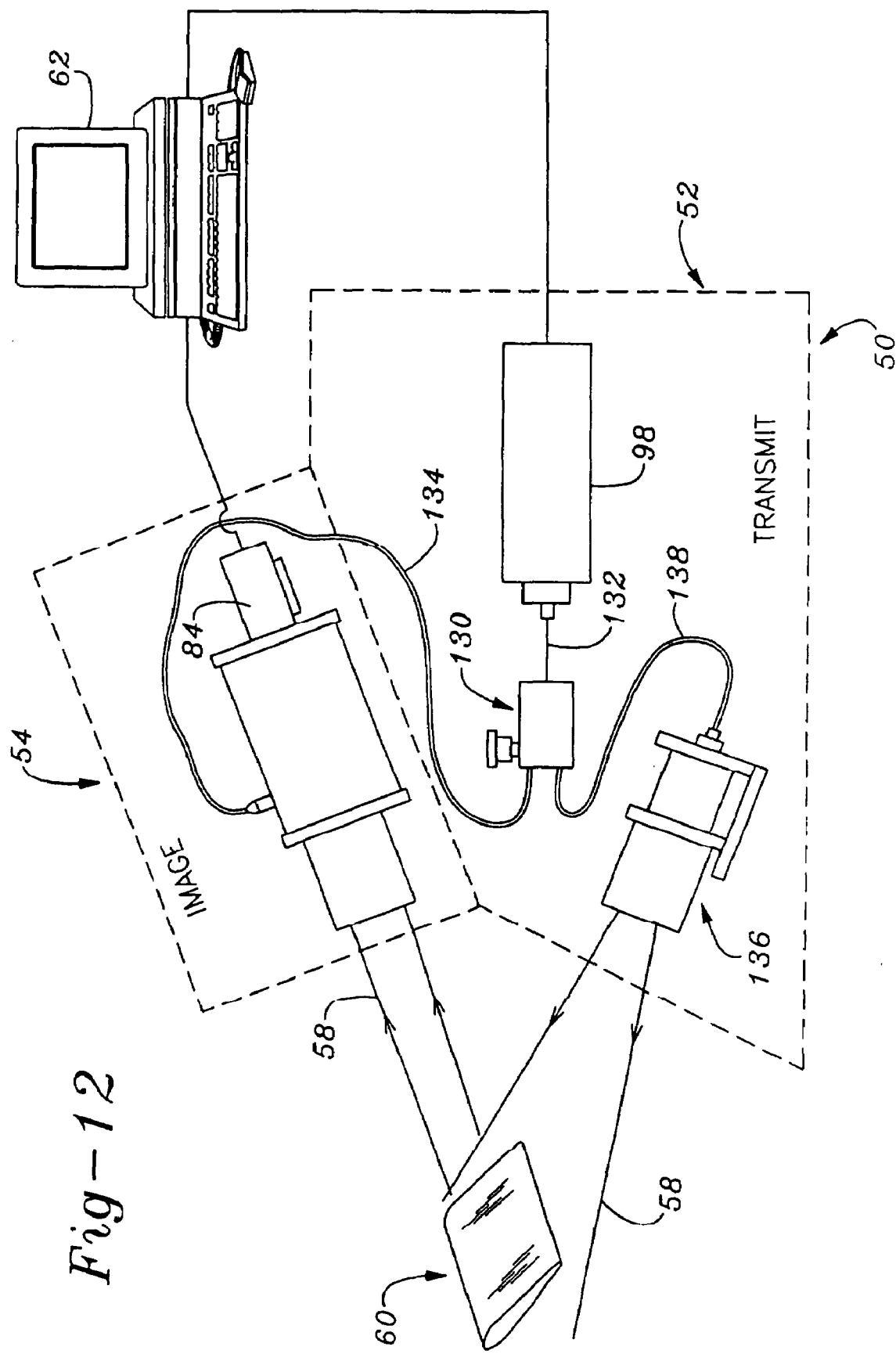

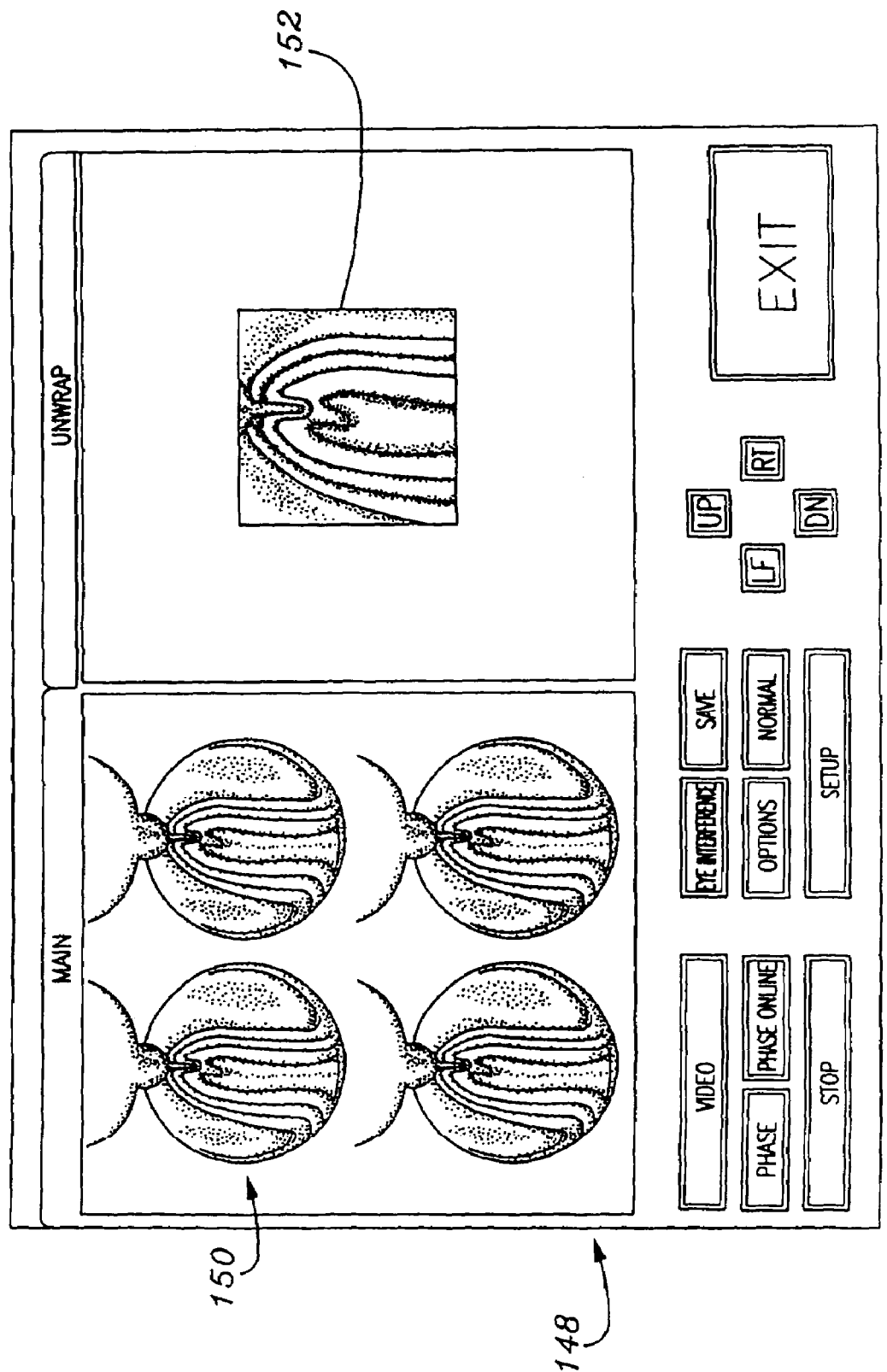

METHODS AND APPARATUS FOR SPLITTING, IMAGING, AND MEASURING WAVEFRONTS IN INTERFEROMETRY

CROSS-REFERENCE TO RELATED APPLICATIONS

The present application is a divisional application of U.S. patent application Ser. No. 10/251,729 filed Sep. 21, 2002, now U.S. Pat. No. 7,170,611, which application is a continuation of U.S. patent application Ser. No. 09/906,542 filed Jul. 16, 2001, and issued as U.S. Pat. No. 6,552,808 on Apr. 22, 2003, which application is a continuation of U.S. patent application Ser. No. 09/413,829 filed Oct. 6, 1999, and issued as U.S. Pat. No. 6,304,330 on Oct. 16, 2001.

STATEMENT REGARDING FEDERALLY SPONSORED RESEARCH

This invention was made with Government support under Contract No. DMI-9531391 awarded by the National Science Foundation. The Government has certain rights in this invention.

BACKGROUND OF THE INVENTION

1. Field of the Invention

The present invention relates to interferometry. More particularly, the present invention relates to methods and apparatus for imaging wavefronts. The methods and apparatus of the present invention may be implemented in measuring systems that measure various parameters of test objects by simultaneously generating a plurality of phase-shifted interferograms.

2. Description of the Related Art

Phase-shift interferometry is an established method for measuring a variety of physical parameters ranging from the density of gasses to the displacement of solid objects. Interferometric wavefront sensors can employ phase-shift interferometers to measure the spatial distribution of relative phase across an area and, thus, to measure a physical parameter across a two-dimensional region. An interferometric wavefront sensor employing phase-shift interferometry typically consists of a spatially coherent light source that is split into two wavefronts, a reference wavefront and an object wavefront, which are later recombined after traveling different optical paths of different lengths. The relative phase difference between the two wavefronts is manifested as a two-dimensional intensity pattern known as an interferogram. Phase-shift interferometers typically have an element in the path of the reference wavefront which introduces three or more known phase steps or shifts. By detecting the intensity pattern with a detector at each of the phase shifts, the phase distribution of the object wavefront can be quantitatively calculated independent of any attenuation in either of the reference or object wavefronts. Both continuous phase gradients and discontinuous phase gradients (speckle waves) can be measured using this technique.

Temporal phase shifting using methods such as piezo-electric driven mirrors have been widely used to obtain high-quality measurements under otherwise static conditions. The measurement of transient or high-speed events requires either ultra high-speed temporal phase shifting (i.e., much faster than the event timescales), which is limited due to detector speed, or spatial phase shifting that can acquire essentially instantaneous measurements.

Several methods of spatial phase shifting have been disclosed in the prior art. In 1983 Smythe and Moore described a spatial phase-shifting method in which a series of conventional beam splitters and polarization optics are used to produce three or four phase-shifted images onto as many cameras for simultaneous detection. A number of United States patents, such as U.S. Pat. Nos. 4,575,248; 5,589,938; 5,663,793; 5,777,741; and 5,883,717, disclose variations of the Smythe and Moore method where multiple cameras are used to detect multiple interferograms. One of the disadvantages of these methods is that multiple cameras are required and complicated optical arrangements are need to produce the phase-shifted images, resulting in expensive complex systems.

Other methods of spatial phase shifting include the use of gratings to introduce a relative phase step between the incident and diffracted beams, an example of which is disclosed in U.S. Pat. No. 4,624,569. However, one of the disadvantages of these grating methods is that careful adjustment of the position of the grating is required to control the phase step between the beams.

Spatial phase shifting has also been accomplished by using a tilted reference wave to induce a spatial carrier frequency to the pattern, an example of which is disclosed in U.S. Pat. No. 5,155,363. This method requires the phase of the object field to vary slowly with respect to the detector pixels; therefore, using this method with speckle fields requires high magnification.

Yet another method for measuring the relative phase between two beams is disclosed in U.S. Pat. No. 5,392,116, in which a linear grating and four detector elements are used. This method has a number of drawbacks, including the inability to measure of wavefronts (i.e., the spatial phase distribution across the profile of a beam) and to form contiguous images on a single pixilated detector such as a standard charge coupled device (CCD).

Finally, it is noted that wavefront sensing can be accomplished by non-interferometric means, such as with Shack-Hartmann sensors which measure the spatially dependent angle of propagation across a wavefront. These types of sensors are disadvantageous in that they typically have much less sensitivity and spatial resolution than interferometric wavefront sensors and are not capable of performing relative phase measurements such as two-wavelength interferometry.

BRIEF SUMMARY OF THE INVENTION

It is one object of the present invention to provide an interferometric wavefront sensor that incorporates spatial phase shifting but avoids the complexity of multi-camera systems by using a single two-dimensional pixilated detector, such as a standard charge coupled device (CCD) camera.

It is another object of the present invention to provide methods and apparatus for performing two-wavelength interferometry that utilize a compact spatial phase-shifting device to acquire data at high speeds and provide improved tolerance to vibration.

It is yet another object of the invention to provide methods and apparatus for dividing an incoming wavefront into four sub-wavefronts that are imaged substantially contiguous to maximize the coverage of a pixilated area detector, while minimizing the number of necessary optical components to provide a compact system.

It is still another object of the invention to provide methods and apparatus for introducing a phase shift between orthogonally polarized reference and object wavefronts that is uniform across each sub-wavefront and not sensitive to the positioning of a diffractive optical element.

According to one aspect of the invention, apparatus for splitting a wavefront and producing four substantially contiguous images of the wavefront consists of an input plane, a first lens element, a diffractive optical element, a second lens element, and an output plane. The lens elements are placed in a telescopic arrangement (separated by the sum of their focal lengths) and the diffractive optical element is placed at or near the mutual focal points. The diffractive optical element produces four output wavefronts (or beams) from a single input wavefront. In a preferred embodiment the diffractive element produces four diffracted orders of equal intensity and symmetric to the incident axis so that it can be characterized by a single divergence angle $\alpha$ and a radial angular spacing of $\beta$. The diffractive optic is constructed to suppress the zero order component to the greatest extent possible. Alternatively, the diffractive optical element may produce three diffracted orders each of equal intensity with the transmitted zero order beam. The diffractive optic may include a wedged substrate to provide a uniform angular tilt to all four beams so they propagate symmetrically to the axis of the incident beam. Again, the compound diffractive optical element is characterized by a single divergence angle $\alpha$ and a radial angular spacing $\beta$. Any higher-order diffracted components from the diffractive optic should be at least twice the angular divergence. The focal length of the second lens may be selected to be equal to the detector size divided by two times the tangent of the diffractive optic's divergence angle. The front lens may be chosen to produce an overall system magnification equivalent to the original wavefront dimension divided by half the detector size.

According to another aspect of the invention, apparatus for introducing a uniform phase-shift between orthogonally polarized reference and object wavefronts includes a polarization mask made of discrete sections. Each section includes a phase retardation plate or a blank and a linear polarizer. The relative angular orientation of the phase retardation plate and linear polarizer is selected to be different for each discrete section. In one exemplary embodiment, the mask element includes four quadrants each providing a phase shift of $\pi/2$ relative to the clockwise adjacent quadrant.

According to still another aspect of the present invention, a system for providing an improved wavefront sensor includes a wavefront splitting element, a polarization mask element, a pixilated detector element, a polarization interferometer, and a computer. The phase of an object beam can be measured with a single frame of data acquired from the pixilated detector.

Yet another aspect of the invention provides a two-wavelength interferometer including a wavefront sensor with a tunable laser or multiple laser sources. Multiple wavefronts are measured at each of several wavelengths with the relative phase values subtracted to determine the contour of an object.

Other objects, features, and advantages of the present invention will become apparent to those skilled in the art from a consideration of the following detailed description taken in conjunction with the accompanying drawings.

BRIEF DESCRIPTION OF THE SEVERAL VIEWS OF THE DRAWINGS

FIG. 1 is a schematic view of measurement apparatus configured in accordance with the present invention, particularly illustrating the measurement apparatus with the use of functional blocks;

FIG. 5 is a schematic view of an exemplary embodiment of measurement apparatus of the invention, particularly illustrating transmit and image portions thereof;

FIG. 10 is a schematic view of another exemplary embodiment of measurement apparatus of the invention, particularly illustrating apparatus for performing profilometry;

FIG. 11 is a schematic view of the measurement apparatus of FIG. 6, particularly illustrating an exemplary commercial embodiment of the profilometer of the invention;

FIG. 12 is a schematic view of a yet another exemplary embodiment of measure apparatus of the invention, particularly illustrating apparatus for measuring displacement;

FIG. 14 is a schematic view of a graphical user interface illustrating interferometric data according to the present invention.

DETAILED DESCRIPTION OF THE INVENTION

Figure 2:
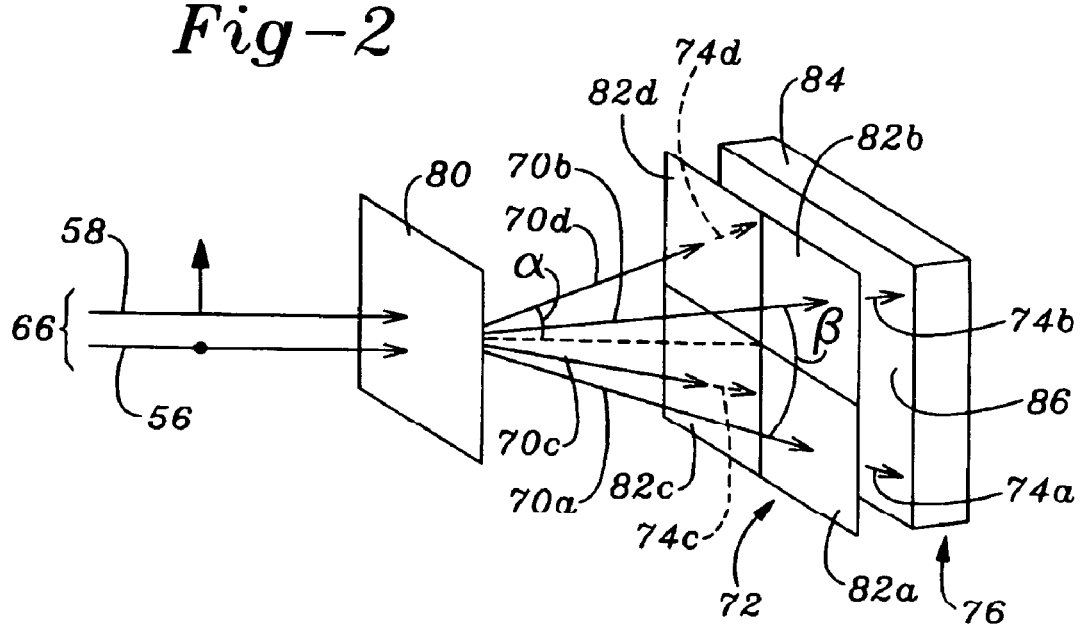
FIG. 2 is a schematic perspective view of an exemplary embodiment of apparatus for generating multiple phase-shifted images in accordance with the present invention.

The present invention provides apparatus and methodology for measuring various parameters of test objects by simultaneously generating multiple phase-shifted images. More particularly, the apparatus and methodology of the present invention enable multiple phase-shifted images (or interferograms) to be obtained with a single imaging device and by a single pulse of a laser and at very high rates. In doing so, the present invention splits, images, and measures a wavefront made up of a reference and an object wavefront from an object under test.

The apparatus of the present invention may be configured to measure—in situ and in real time—flow parameters in a multiphase environment. Examples of such flow parameters include the concentrations of selected gaseous species, temperature distributions, particle and droplet distributions, density, and so on. In addition to flow parameters, the apparatus of the present invention may be configured to measure the displacement (e.g., the vibration) of an object. Moreover, the apparatus of the invention may be configured to perform profilometry of an object, that is, to measure the absolute three-dimensional profiles of solid objects. These and other utilizations and embodiments of the technology of the present invention are discussed in detail herein.

Turning to the drawings, a measurement system 50 exemplifying the principles of the present invention is illustrated in FIG. 1. Exemplary measurement system 50 generally includes a transmit portion 52 and an image portion 54. The transmit portion 52 transmits a reference wavefront 56 to the image portion 54 and an object wavefront 58 to an object 60 under measurement. The reference and object wavefronts 56 and 58 are preferably generated by a spatially coherent light source such as a laser. The object wavefront 58 is received by the image portion 54 after acting upon the object 60, for example, by reflection or by transmission. Data obtained by the image portion 54 from the object 60 may be provided to a computer 62 for processing. The transmit portion 52 and the image portion 54 may be oriented with respect to the object 60 according to a plurality of measurement configurations, which are discussed in detail below.

With continued reference to FIG. 1, exemplary image portion generally includes a wavefront-combining element 64 for receiving the reference wavefront 56 and the object wavefront 58 and for combining the wavefronts into a combined wavefront 66. The reference and object wavefronts 56 and 58 are combined to be superimposed and orthogonally polarized, which is discussed below. A wavefront-splitting element 68 receives the combined wavefront 66 and splits the wavefront into a plurality of sub-wavefronts 70. A phase-shifting interference element 72 receives the sub-wavefronts 70 and is configured to shift the relative phase between the reference and object wavefronts 56 and 58 and to interfere the reference and object wavefronts 56 and 58 by polarization, for each of the sub-wavefronts 70, to yield a plurality of phase-shifted interferograms 74. A sensing element 76 receives the phase-shifted interferograms 74 from the phase-shifting interference element 72 substantially simultaneously. The sensing element 76 provides data 78 indicative of the interferograms 74 to the computer 62 for processing.

According to the present invention, the phase-shifting interference element 72 shifts the relative phase between the reference and object wavefronts 56 and 58 for each of the sub-wavefronts 70 discretely by a factor of a predetermined amount p. The predetermined amount p may be determined by a number N of sub-wavefronts 70 in the plurality of sub-wavefronts generated by the wavefront-splitting element 68 from the combined wavefront 66. For example, the predetermined amount p may be determined as the quotient of 360 degrees and the number N of sub-wavefronts 70, or:

$$p = 360° \div N. \quad (1)$$

Accordingly, the discrete phase shift $\Delta\phi$ of each of the plurality of sub-wavefronts 70 may be determined as:

$$\Delta\phi_i = (i-1) \times p, \quad (2)$$

where i=1 to N. For example, if the wavefront-splitting element 68 provides four sub-wavefronts 70, then the discrete phase shifts $\Delta\phi$ of the four wavefronts are 0°, 90°, 180°, and 270°. According to this embodiment, there is a 90° phase shift between each of the interferograms 74.

An exemplary embodiment of the combination of the wavefront-splitting element 68, the phase-shifting interference element 72, and the sensing element 76 is illustrated in FIG. 2. As shown, the combined wavefront 66 includes the reference wavefront 56 from the transmit portion 52 and the object wavefront 58 from the object 60. The wavefront-combining element 64 is configured so that the reference wavefront 56 and the object wavefront 58 are orthogonally polarized, which is indicated in FIG. 2 by the scientific convention of an arrow and a dot. Exemplary wavefront-splitting element 68 is preferably a two-dimensional diffractive optical element (DOE) such as a holographic optical element (HOE) 80. According to a preferred embodiment of the invention, exemplary DOE 80 splits the combined wavefront 66 into four sub-wavefronts 70a, 70b, 70c, 70d. Each of the sub-wavefronts 70a-70d follows a spatially discrete path.

With continued reference to FIG. 2, exemplary phase-shifting interference element 72 includes a plurality of sections 82, the number of which preferably equals the number N of sub-wavefronts 70 provided by the wavefront-splitting element 68. According to the preferred embodiment shown, exemplary phase-shifting interference element 72 includes four sections 82a, 82b, 82c, 82d. The phase-shifting interference element 72 is disposed with respect to the wavefront-splitting element 68 so that the plurality of sub-wavefronts 70 are respectively incident on the plurality of sections 82; that is, each section 82 receives one of the sub-wavefronts 70. As discussed above, each of the sections 82 shifts the relative phase between the reference and object wavefronts 56 and 58 and interferes the two wavefronts 56 and 58 for each of the sub-wavefronts 70 incident thereon by a discrete phase shift $\Delta\phi_i$. Each of the sections 82a, 82b, 82c, . . . 82N of the phase-shifting interference element 72 accordingly provides a respective phase-shifted interferograms 74a, 74b, 74c, . . . , 74N. The phase of each phase-shifted interferogram 74 is out of phase with the phase of the other phase-shifted interferograms 74 by a factor of the predetermined amount p of phase shift, which is discussed further below.

Continuing to reference FIG. 2, exemplary sensing element 76 is preferably an imaging sensor or a detector array 84. The detector array 84 may be a video-imaging sensor such as a charged coupled device (CCD) camera. According to the present invention, the detector array 84 preferably has an active surface 86. The active surface 86 may be defined by a pixel array. The detector array 84 may be made from a plurality of individual detector arrays configured to function as a single active sensing element. For example, the active surface 86 may be defined by more than one CCDs collectively functioning as a single array. For the purposes of this description, the active surface 86 has a surface area S.

The detector array 84 is disposed with respect to the phase-shifting interference element 72 so that the plurality of phase-shifted interferograms 74 are substantially simultaneously incident on the active surface 86, thereby imaging on the active surface 86 a respective plurality of phase-shifted interferograms. Based on the imaged interferograms, the spatially resolved phase of each of the phase-shifted interferograms 74 can be measured instantaneously. In addition, the detector array 84 is disposed with respect to the phase-shifting interference element 72 so as to maximize the area of the active surface 86, which is discussed in more detail below.

Figure 3:
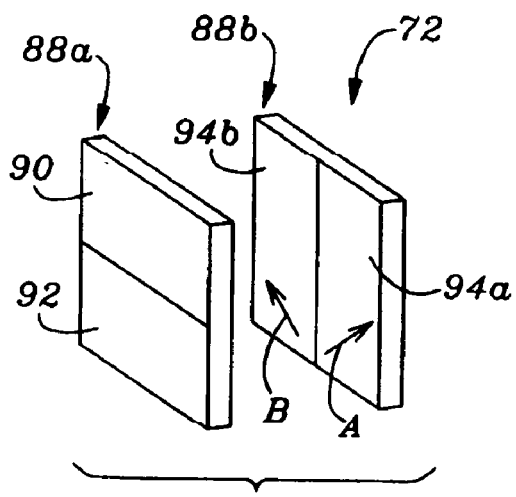
FIG. 3 is a schematic perspective view of an exemplary phase-retardant plate according to the invention, particularly illustrating a phase-retardant plate for shifting the phase of four wavefronts.

With additional reference to FIG. 3, an exemplary embodiment of the phase-shifting interference element 72 includes a plurality of plates 88. For the preferred four-component embodiment described above, exemplary phase-shifting interference element 72 includes a first plate 88a and a second plate 88b. For purposes of clarity and illustration, the plates 88 are shown in a spaced relationship; however, according to exemplary embodiments of the invention, the plates 88 are substantially planar, disposed in a parallel relationship, and abut each other. The first plate 88a includes a quarter-wave plate 90 and a blank plate 92. As known in the art, a quarter waveplate shifts the relative phase of two orthogonally polarized incident wavefronts by 90°, and a blank plate shifts the relative phase of two orthogonally polarized incident wavefronts by 0° (i.e., there is no relative phase shift). The plates 90 and 92 are preferably coplanar and divide the first plate 88a into respective halves.

The second plate 88b of exemplary phase-shifting interference element 72 includes a pair of polarizing plates 94a and 94b that are configured to polarize an incident wavefront linearly so that electric field vectors of the transmitted wavefront are perpendicular with each other. Specific to the illustrated embodiment, one of the polarizing plates, e.g., plate 94a, is configured to polarize light at +45° with respect to the vertical axis (as shown by arrow A in FIG. 3), thereby interfering the in-phase components of the reference and object wavefronts 56 and 58. The other polarizing plate, e.g., plate 94b, is configured to polarize light at −45° with respect to the vertical axis (as shown by arrow B in FIG. 3), thereby interfering the out-of-phase components of the reference and object wavefronts 56 and 58. The polarizing plates 94a and 94b are preferably coplanar and divide the second plate 88b into respective halves.

Figure 4:
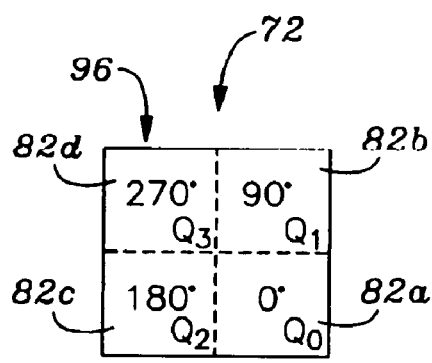
FIG. 4 is a plan view of the phase-retardant plate shown in FIG. 3.

With continued reference to FIG. 3 and additional reference to FIG. 4, the first and second plates 88a and 88b are configured so that the respective halves thereof are perpendicular with each other, thus forming a phase-retardation mask or plate 96. In the four-component embodiment shown, the phase-retardation plate 96 includes four sections 82, each of which defines a quadrant. Section 82a, or quadrant $Q_0$, is defined by the blank plate 92 and polarizing plate 94a, thus interfering the in-phase (i.e., 0°) component between the incident reference and object wavefronts 56 and 58. Section 82b, or quadrant $Q_1$, is defined by the quarter-wave plate 90 and polarizing plate 94a, thus interfering the in-phase quadrature (i.e., 90°) component between the incident reference and object wavefronts 56 and 58. Section 82c, or quadrant $Q_2$, is defined by the blank plate 92 and polarizing plate 94b, thus interfering the out-of-phase (i.e., 180°) component between the incident reference and object wavefronts 56 and 58. And section 82d, or quadrant $Q_3$, is defined by the quarter-wave plate 90 and polarizing plate 94b, thus interfering the out-of-phase quadrature (i.e., 270°) component between the incident reference and object wavefronts 56 and 58.

The operation of the phase-shifting interference element 72 may be described with respect to the reference and object wavefronts 56 and 58 which, as mentioned above, are orthogonally polarized. The electric field vectors for each of the wavefronts 56 and 58 may be written as:

$$\bar{E}_r = Re^{i(kz-\omega t)}\hat{s} \tag{3a}$$

$$\bar{E}_s = Se^{i(kz-\omega t+\Delta\phi)}\hat{p} \tag{3b}$$

where:
R and S are the amplitudes of each wavefront 56 and 58, respectively;
ω is the optical frequency;
t is time;
k is the wavevector=$2\pi/\lambda$;
p and s are orthogonal unit polarization vectors; and
ΔΦ is the phase difference between the wavefronts 56 and 58.

The intensity (I) of each of the phase-shifted interferograms 74 incident on the active surface 86 of the detector array 84 is given by:

$$I_0 = \frac{1}{2}\left(I_r + I_s + 2\sqrt{I_r I_s}\cos(\Delta\phi)\right) \tag{4a}$$

$$I_1 = \frac{1}{2}\left(I_r + I_s + 2\sqrt{I_r I_s}\cos\left(\Delta\phi + \frac{\pi}{2}\right)\right) \tag{4b}$$

$$I_2 = \frac{1}{2}\left(I_r + I_s + 2\sqrt{I_r I_s}\cos(\Delta\phi + \pi)\right) \tag{4c}$$

$$I_3 = \frac{1}{2}\left(I_r + I_s + 2\sqrt{I_r I_s}\cos\left(\Delta\phi + \frac{3\pi}{2}\right)\right) \tag{4d}$$

where $I_r$ and $I_s$ are the intensities of the reference and object wavefronts 56 and 58, respectively (which intensities are proportional to $R^2$ and $S^2$). This set of phase-shifted intensities $I_0$, $I_1$, $I_2$, and $I_3$ may be analyzed numerically using a number of algorithms to solve explicitly for the phase difference between the reference and object wavefronts 56 and 58, which is discussed in detail below.

As it is preferable to maximize the imaging area of the detector array 84 (i.e., to maximize the portion of the surface area S of the active surface 86 that is illuminated by the interferograms 74), the phase-retardation plate 96 is preferably disposed adjacent to or substantially at the active surface 86 of the detector array 84, which is discussed in more detail below. By detecting the plurality of phase-shifted interferograms 74 instantaneously with an imaging sensor exemplified by the detector array 84, the image portion 54 of the invention enables the measuring system 50 to instantaneously measure the entire test object 60. In addition, the instantaneous detection of the phase-shifted interferograms 74 eliminates the need to scan individual beams spatially through or across the surface of the object 60.

As mentioned above, exemplary measurement system 50 of the present invention may be configured in a plurality of preferred embodiments each designed to carry out a particular type of real-time measurement, including a profilometer, a displacement sensor, and a wavefront sensor. In other words, exemplary embodiments of the measuring system 50 include a common transmit portion 52 and a common image portion 54 that can be physically oriented in a plurality of configurations with a plurality of optical and imaging components to undertake a plurality of measurements, which is discussed in detail below.

FIG. 5 illustrates one such exemplary configuration of the measurement system 50 of the invention which may be used to perform real-time interferometry for measuring transient events. The transmit portion 52 according to this embodiment includes a coherent light source such as a laser or laser diode 98. The laser 98 may include a half-wave plate 100 to provide a coherent light wavefront 102 which is split by a polarizing beam splitter (PBS) 104 into the reference wavefront 56 and the object wavefront 58. The PBS 104 is configured to provide orthogonally polarized wavefronts as shown. The object wavefront 58 is expanded by, for example, a combination of an expanding lens 106 and a collimating lens 108. Upon expansion, the object wavefront 58 is transmitted to the test object 60 where the object wavefront 58 is incident upon the surface or boundary thereof and either reflected from or transmitted through the object 60.

Exemplary image portion 54 receives the object wavefront 58 from the object 60 and may include optics for collimating the received object wavefront 58, such as a combination of a collecting lens 110 and a collimating lens 112. Collimating lens 112 is preferably spaced from the collecting lens 100 by a distance equal to the sum of their respective focal lengths $f_1$ and $f_2$. The object wavefront 58 is then superimposed with the reference wavefront 56 at the wavefront-combining element 64 which may be a polarizing beam splitter (PBS) 114 to yield the combined wavefront 66. PBS 114 is preferably spaced from collimating lens 112 by a focal length $f_2$ of the collimating lens. The combined wavefront 66 may be focused on the diffractive optical element 80 by means of a convex lens 116. In turn, the plurality of sub-wavefronts 70 may be focused on the phase-retardation/interference plate 96 either directly or by means of a collimating lens 118 as shown.

The placement of the various elements with respect to each other is chosen to maximize the operability of the image portion 54. For example, PBS 114, the convex lens 116, and the diffractive optical element 80 are preferably respectively spaced apart by focal length $f_3$, which is the focal length of the convex lens 116. In addition, the diffractive optical element 80, the collimating lens 118, and the phase-retardation/interference plate 96 are preferably respectively spaced apart by a focal length $f_4$, which is the focal length of the collimating lens 118. The placement of the diffractive optical element 80 at the focus of collimating lens 118, which is defined as the input focal plane or the Fourier transform plane, optimizes the area of the active surface 86 of the detector array 84 illuminated by the plurality of phase-shifted interferograms 74.

Figure 6:
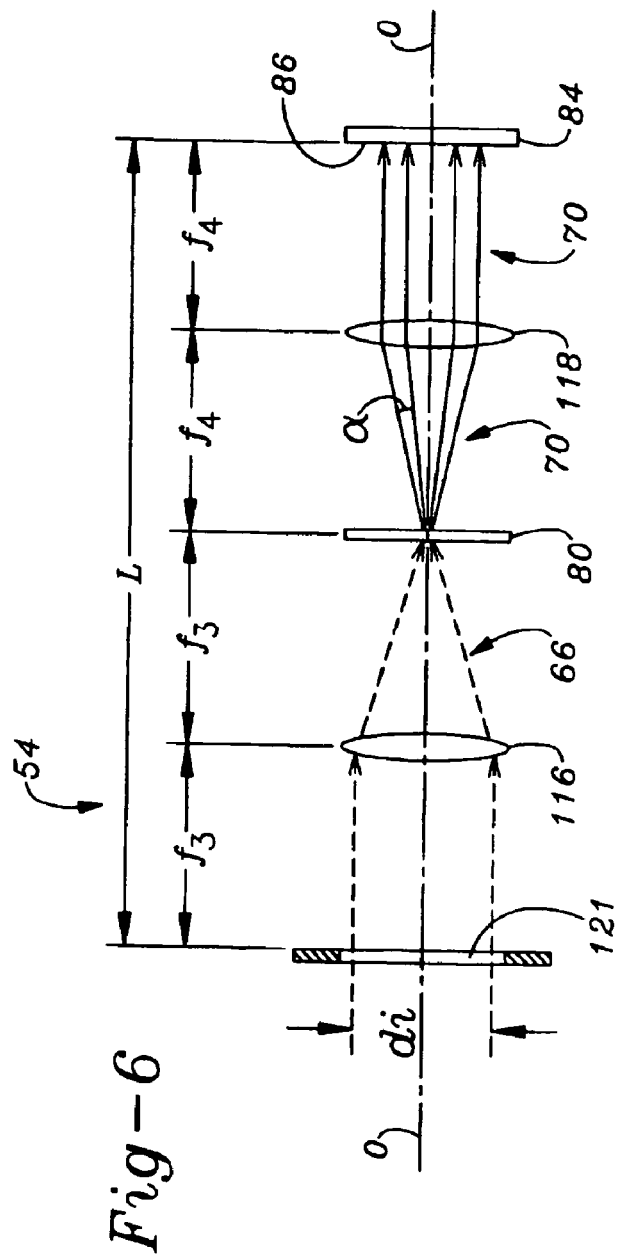
FIG. 6 is a schematic view of an exemplary embodiment of an image portion of the measurement apparatus of the invention.

Referencing FIG. 6, the optics of exemplary imaging portion 54 are shown in more detail. The optical elements of the imaging portion 54 are aligned along an optical axis O. As mentioned above, the diffractive optical element 80 splits the combined wavefront 66 into a plurality of (e.g., four) sub-wavefronts 70. Each of the sub-wavefronts 70 follows an optical path defined by the distance each of the sub-wavefronts 70 follows from the diffractive optical element 80 to the active surface 86 of the detector array 84.

Figure 7:
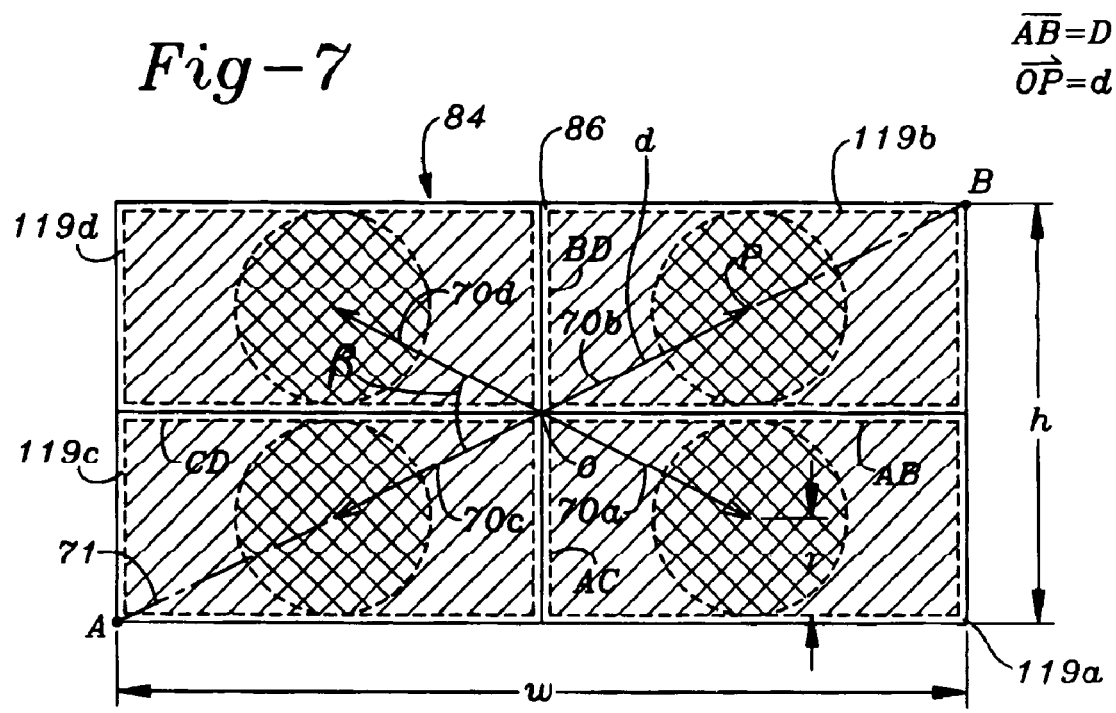
FIG. 7 is a schematic view of an active surface of a detector array of an image portion of the present invention, particularly illustrating an exemplary plurality of sub-wavefronts coaxial along an optical axis of the image portion.
Figure 8:
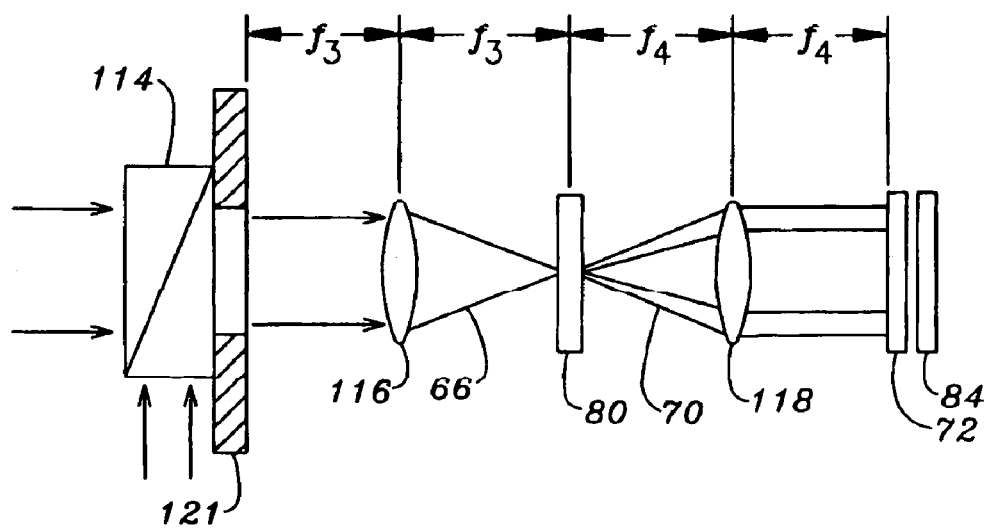
FIG. 8 is a schematic view of another exemplary embodiment of an imaging portion of the present invention, particularly illustrating the inclusion of a polarizer and a mask.

The diffractive optical element 80 and lenses 116 and 118 are configured so that each of the imaged sub-wavefronts 70 incident at detector surface 86 are adjacent to or substantially contiguous with at least one other sub-wavefront, which is shown in FIG. 7. For example, in the exemplary embodiment shown, sub-wavefront 70a is substantially contiguous with sub-wavefronts 70b and 70c, which is respectively indicated by reference alphas AB and AC; sub-wavefront 70b is substantially contiguous with sub-wavefronts 70a and 70d, which is respectively indicated by reference alphas AB and BD; sub-wavefront 70c is substantially contiguous with sub-wavefronts 70a and 70d, which is respectively indicated by reference alphas AC and CD; and sub-wavefront 70d is substantially contiguous with sub-wavefronts 70b and 70c, which is respectively indicated by reference alphas BD and CD. This substantially contiguous nature of the sub-wavefronts 70 is further enhanced in an embodiment in which the diffractive optical element 80 splits the combined wavefront 66 into a plurality of sub-wavefronts having a substantially rectangular cross section as shown in FIG. 8.

The exemplary diffractive optical element 80 preferably splits the combined wavefront 66 in such a manner that the sub-wavefronts 70 diverge from the optical axis O at substantially equal angles. In a preferred embodiment, the diffractive optical element 80 may produce four diffracted orders that have equal intensity and are symmetric to the incident axis so that the diffracted orders may be characterized by a single divergence angle α and a radial angular displacement β. The diffractive optical element 80 may be constructed to suppress the zero order component to the greatest extent possible.

In another exemplary embodiment, the diffractive optical element 80 may produce three diffracted orders each of equal intensity with the transmitted zero order beam. The diffractive optical element 80 may include a wedged substrate to provide a uniform angular tilt to all four beams so that the beams propagate symmetrically to the axis of the incident beam. As mentioned above, the diffractive optical element 80 is preferably characterized by a single divergence angle α and a radial angular displacement β.

Referring to FIG. 7, the radial angular displacement β produced by exemplary diffractive optical element 80 is determined by the aspect ratio of the height h and the width w of the active surface 86 of the detector array 84. The desired radial angular displacement β is given by:

$$\beta = 2\tan^{-1}\left(\frac{h}{w}\right) \tag{5}$$

where w and h are the width and the height of the active surface 86 of detector array 84. For a detector with a unity aspect ratio (i.e., square), the radial angular displacement β becomes 90 degrees and all four images are radially symmetric.

Accordingly, each of the sub-wavefronts 70 follows an independent optical path from the diffractive optical element 80 to the active surface 86 that has a length substantially equal to each of the other optical paths. As such, the plurality of sub-wavefronts 70 reach the active surface 86 substantially simultaneously. By configuring the imaging portion 54 so that the sub-wavefronts 70 have substantially equal optical path lengths, the imaging portion 54 is less susceptible to errors that may introduced by vibration to the system.

With particular reference to FIG. 7, exemplary active surface 86 of the detector array 84 may have a plurality of sections 119 for respectively receiving the plurality of sub-wavefronts 70. Each of the sections 119 has a surface area on which the respective sub-wavefront 70 is incident. According to the present invention, the portion or percentage of the surface area of each section 119 on which a sub-wavefront is incident is preferably maximized, thereby maximizing the resolution of the detector array 84. For example, each of the sub-wavefronts 70a-70d is incident on at least half of the surface area of a respective section 119a-119d. More preferably, the percentage is at least 75%. In the embodiment shown in FIG. 7 by the circular cross-hatched regions, the incident percentage of each sub-wavefront 70 may be determined by $\pi r^2$ divided by $(h/2+w/2)^2$. In the embodiment shown in FIG. 7 by the rectangular cross hatched region, the incident percentage of each sub-wavefront is substantially 100%.

Figure 9:
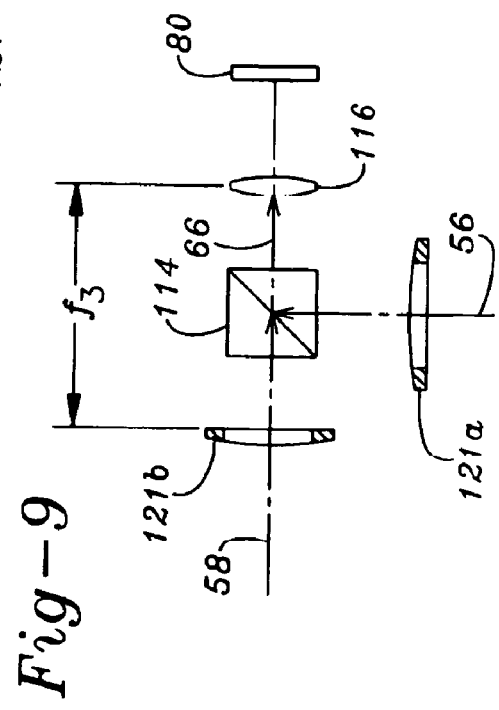
FIG. 9 is a schematic view illustrating an exemplary imaging portion of the invention.

Further referencing FIG. 6 and with addition reference to FIG. 8, an aperture 121 may be provided at an input focal plane of the convex lens 116 (i.e., at a focal length $f_3$), with the diffractive optical element 80 positioned at the output focal plane of the convex lens 116. Alternatively, as shown in FIG. 9, a pair of apertures 121a and 121b may be positioned upstream of PBS 114 through which the reference and object wavefronts 56 and 58 respectively travel. According to a preferred embodiment of the invention, the aperture(s) 112 may be rectangular with an aspect ratio substantially the same as the active surface 86 of the detector array 84. The presence of the aperture(s) 121 reduces the amount of ambient noise received in the image portion 54 and reduces crosstalk between the imaged sub-wavefronts.

An example of a design method that maximizes the surface area coverage follows. With reference to FIGS. 6 and 7, the focal length of lens 118 is selected to be equal to one fourth of the diagonal length D of the active area of detector 84 divided by the tangent of the divergence angle α of the diffractive optical element 80. For illustrative clarity, the diagonal length D is shown as segment AB in FIG. 7. Thus:

$$f_4 = \frac{D}{4\tan\alpha} \quad (6)$$

The front lens 116 is chosen to produce an overall system magnification equivalent to the diagonal length $d_i$ of the input aperture 112 (shown in FIG. 6) divided by the diagonal length D of the detector array 84. Thus:

$$f_3 = \frac{d_i}{D} f_4 \quad (7)$$

The overall length L of the imaging portion 54 is given by:

$$L = 2(f_3 + f_4) = \frac{(d_i + D)}{2\tan\alpha} \quad (8)$$

According to an exemplary embodiment of the invention, the aperture(s) 121 may be selected so that the diagonal length $d_i$ is substantially equal to the diagonal length D of the detector array 84 (i.e., $d_i$=D). According to such an embodiment, focal length $f_3$ is equal to focal length $f_4$ and the overall system length L is given by:

$$L = 2(f_3 + f_4) = \frac{D}{\tan\alpha} \quad (9)$$

It can be seen from Equations 7 and 8 that in many embodiments it is desirable to have a large diffractive optic divergence angle α to reduce the overall size of imaging portion 54. In practice, divergence angles α of 5 degrees to 10 degrees produce a relatively compact system.

In addition to the real-time interferometer embodiment illustrated in FIG. 5, exemplary measurement system 50 of the present invention may be configured in a plurality of additional preferred embodiments each designed to carry out a particular type of real-time measurement, including a profilometer, a displacement sensor, and a wavefront sensor, each of which is described in detail below.

Referencing FIG. 10, exemplary measurement system 50 of the present invention is configured to perform profilometry. Exemplary profilometer 50 is configured to perform on-axis illumination and viewing, which is useful in obtaining three-dimensional (3D) information of the object 60. Many industries utilize profilometry in research and development, quality control, and manufacturing, including the semiconductor and medical industries.

Exemplary transmit portion 52 includes the laser 98 which transmits the coherent light wavefront 102. A single polarizing wavefront splitter (PBS) 120 is shared by both the transmit and image portions 52 and 54 for splitting the light wavefront 102 into the reference wavefront 56 and the object wavefront 58 and combining the reference wavefront 56 and the object wavefront 58 into the combined wavefront 66. In addition to PBS 120, exemplary image portion 54 of the profilometer includes the convex lens 116, the diffractive optical element 80, the collimating lens 118 displaced from element 80 by its focal length, the phase-retardation/-interference plate 96, and the CCD camera. The computer 62 may be connected to both the transmit and image portions 52 and 54 to control the operation of the laser 98 and to receive imaging data 78 from the detector array 84.

FIG. 11 illustrates an exemplary commercial embodiment of the profilometer 50 of FIG. 10. As shown, the laser 98 provides the light wavefront to an integrated measuring unit 122 by means of an optical cable 124. The integrated measuring unit 122 includes a housing 126 in which the common PBS 120, as well as each of the elements of the image portion 54 shown in FIG. 9, is received. The integrated measuring unit 122 transmits and receives the object wavefront 58, with the detector array 84 providing image data to the computer 62 via a cable 128.

Referencing FIG. 12, another exemplary commercial embodiment of the measurement system 50 of the present invention is shown and configured to function as a displacement sensor. Displacement sensors are useful in measuring, for example, the vibration or the strain of an object. Exemplary transmit portion 52 of the displacement-sensor embodiment of the measuring system 50 includes the laser 98 which transmits the coherent light wavefront to a fiber wavefront splitter 130 via an optical cable 132. The fiber wavefront splitter 130 splits the light wavefront into the reference wavefront 56, which is provided to the image portion 52 by an optical cable 134, and the object wavefront 58, which is provided to an optics unit 136 by an optical cable 138. The optical unit 136 of the transmit portion 52 includes the wavefront-expanding optics of the concave lens 106 and collimating lens 108 (see FIG. 5). The operation of the displacement sensor illustrated in FIG. 12 is analogous to that described above.

According to the displacement-sensor embodiment of the measurement unit 50, the separate and portable optics unit 136 may be positioned relative to the test object 60 and the image portion 54. The object wavefront 58 can thus be directed to the object 60 from any angle or position.

Figure 13:
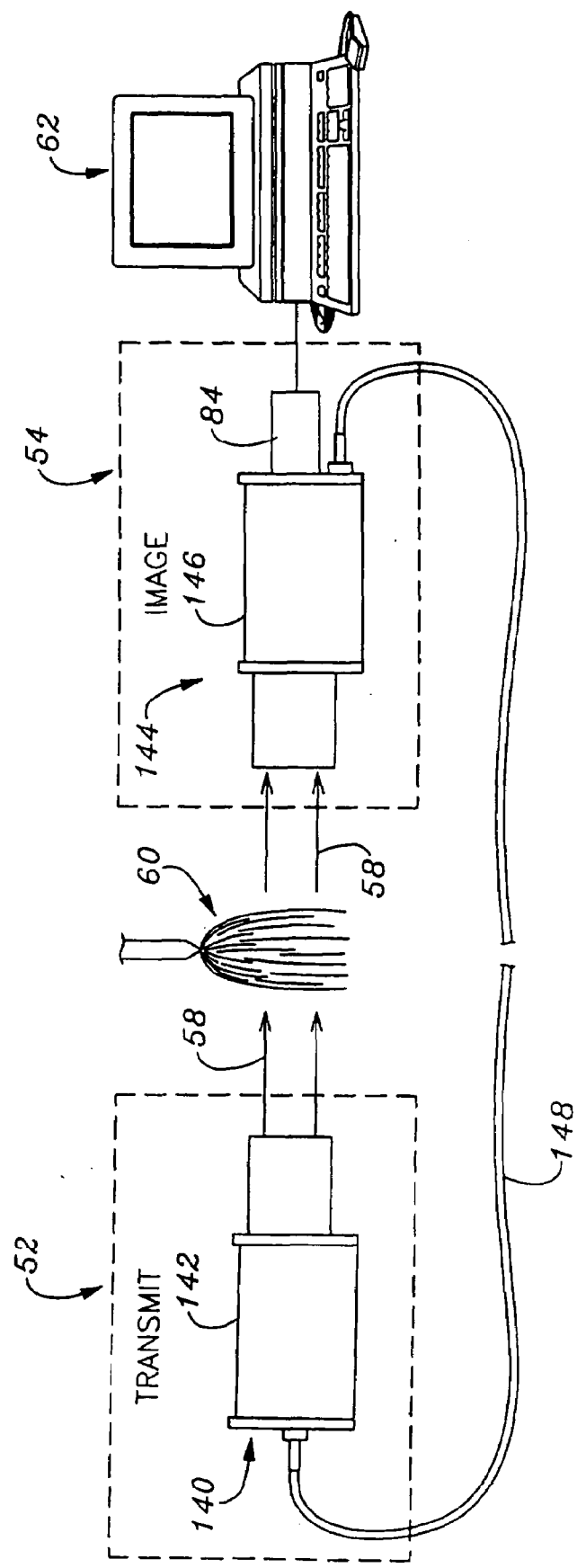
FIG. 13 is a schematic view of still another exemplary embodiment of the measurement apparatus of the invention, particularly illustrating apparatus for performing wavefront sensing.

Referencing FIG. 13, yet another exemplary commercial embodiment of the measurement system 50 of the present invention is shown and configured to function as a wavefront sensor. Wavefront sensors may be used to measure, for example, pressure, temperature, or density gradients in transparent solids, liquids, or gases. Exemplary transmit portion 52 may include an integrated transmit unit 140 with a housing 142, and exemplary image portion 54 may include an integrated receive unit 144 with a housing 146. Similar to the layout of the measurement system 50 shown in FIG. 5, exemplary transmit unit 140 of the wavefront-sensor embodiment of the measuring system 50 includes the laser which transmits the reference wavefront 56 to the integrated receive unit 144 via an optical cable 148 and the object wavefront 58 to the test object 60. The operation of the wavefront sensor illustrated in FIG. 13 is analogous to that described above.

For each of the foregoing embodiments of the measuring system 50 of the present invention, a software application may be utilized by the computer 62 for data acquisition and processing. The software application causes the computer 62 to acquire, process, analyze, and display data associated with the phase-shifted interferograms 74. Data acquisition may be accomplished by recording two interferograms for each measurement: a reference interferogram for the reference wavefront 56 and an object interferogram for the object wavefront 58. Wrapped phase maps are calculated for each of the interferograms and then subtracted from each other. The result is unwrapped to yield a map of the phase change between the reference and object interferograms. Unwrapping is the procedure used to remove the modulo $2\pi$ ambiguity that is characteristic of interferometric data.

Phase may be calculated based on a single frame of data according to:

$$\Phi(x,y)=\tan^{-1}\{[I_3(x,y)-I_1(x,y)]\div[I_0(x,y)-I_2(x,y)]\}, \qquad (10)$$

where $I_0$, $I_1$, $I_2$, and $I_3$ are the respective intensities of each of the phase-shifted interferograms 74a-74d incident on the active surface 86 of the detector array 84 from the four sections 82a-82d (i.e., quadrants $Q_0$, $Q_1$, $Q_2$, and $Q_3$) as calculated in Equations 4a-4d above. The variables x and y are the pixel coordinates. To reduce noise in the image, spatial averaging may be used to smooth the phase map while retaining a sharp transition at the $2\pi$-0 phase step. The spatially averages phase may be calculated using the following equations:

$$\Phi(x,y)=\tan^{-1}\{\text{sum}(x,y\epsilon\delta)[I_3(x,y)-I_1(x,y)]\div\text{sum}(x,y\epsilon\delta)\\{}[I_0(x,y)-I_2(x,y)]\}, \qquad (11)$$

where the sums are performed over the range of $\delta$ nearest neighbors. Increasing the number of averaged pixels improves smoothness of the phase map at the expense of spatial resolution; however, the sharpness of the phase discontinuity is retained, thereby permitting rapid phase unwrapping. The unwrapping of phase maps removes the discontinuous step and permits quantitative analysis of the images.

The number of pixels averaged may be selected by a user. For comparing two states of the system of to subtract background phase noise from the system, the phase difference mode can be used. Phase may be calculated according to:

$$\Delta\Phi(x,y)=\tan^{-1}[X(x,y)\div Y(x,y)], \qquad (12)$$

where:

$$X(x,y)=[Ib_3(x,y)-Ib_1(x,y)]*[It_0(x,y)-It_2(x,y)]-[It_3(x,y)-It_1(x,y)]*[Ib_0(x,y)-Ib_2(x,y)],$$

$$Y(x,y)=[Ib_0(x,y)-Ib_2(x,y)]*[It_0(x,y)-It_2(x,y)]+[Ib_3(x,y)-Ib_1(x,y)]*[It_3(x,y)-It_1(x,y)],$$

Ib is the baseline image captured, and

It is the image captured for comparison.

Spatial averaging can be accomplished using the formula:

$$\Delta\Phi(x,y)=\tan^{-1}[\text{sum}(x,y\epsilon\delta)X(x,y)\div\text{sum}(x,y\epsilon\delta)Y(x,y)]. \qquad (13)$$

The three dimensional shape of an object can be determined by using two color interferometry. To do so, a first set of four phase-shifted interferograms is captured at a first wavelength $\lambda_1$ (i.e., $Ib_n$), and a second set of phase-shifted interferograms is captured at a second wavelength $\lambda_2$ (i.e., $It_n$). The relative distance to the object (or range) is calculated by:

$$R(x,y)=\frac{\lambda^2}{4\pi\Delta\lambda}\tan^{-1}\left(\frac{X(x,y)}{Y(x,y)}\right), \qquad (14)$$

where:

$$X(x,y)=[Ib_3(x,y)-Ib_1(x,y)]*[It_0(x,y)-It_2(x,y)]-[It_3(x,y)-It_1(x,y)]*[Ib_0(x,y)-Ib_2(x,y)]$$

$$Y(x,y)=[Ib_0(x,y)-Ib_2(x,y)]*[It_0(x,y)-It_2(x,y)]+[Ib_3(x,y)-Ib_1(x,y)]*[It_3(x,y)-It_1(x,y)]$$

Noise in the image can be significantly reduced using a weighted spatial average over neighboring pixels. This can be accomplished by:

$$R(x,y)=\frac{\lambda^2}{4\pi\Delta\lambda}\tan^{-1}\left(\frac{\sum_{x,y\in\delta}X(x,y)}{\sum_{x,y\in\delta}Y(x,y)}\right), \qquad (15)$$

where the sums are performed over the range of $\delta$ nearest neighbors. Because of the modelo $2\pi$ behavior of the arctangent function, the range is wrapped (ambiguous) beyond the so-called synthetic wavelength of:

$$\lambda_s=\frac{\lambda^2}{4\pi\Delta\lambda}. \qquad (16)$$

The well-known process of spatial phase unwrapping can be used to remove the discontinuous steps and to permit quantitative analysis of the images. Alternatively, it is possible to use multiple synthetic wavelengths and incrementally add the range distance as known in the art. The overall range is then given by:

$$R'(x,y)=\sum_m\frac{R_{\Delta\lambda m}(x,y)}{m}, \qquad (17)$$

where m is the number of wavelength steps used and $R_{\Delta\lambda m}$ is the range measured with a frequency tuning of $\Delta\lambda/m$. Implied in this method is that no single measurement should have a phase value greater than $2\pi$, which can place a restriction on the maximum size of the object that can be measured.

Referencing FIG. 14, a user interface 148 provided by the software of the invention is shown displaying a raw interferogram 150 and wrapped phasemaps 152 from a central portion of the raw interferogram 150. The raw interferogram 150 illustrates data 78 resulting from the measurement of a diffusion flame.

Those skilled in the art will understand that the preceding exemplary embodiments of the present invention provide the foundation for numerous alternatives and modifications thereto. These other modifications are also within the scope of the present invention. Accordingly, the present invention is not limited to that precisely as shown and described above.

What is claimed is:

1. A method for sensing a wavefront with a sensing element including an active surface having a plurality of sections each with a surface area, the method comprising splitting the wavefront into four sub-wavefronts wherein each of the sub-wavefronts illuminates substantially 100% of the surface area of a respective one of the sections of the active surface.

2. The method of claim 1 further comprising simultaneously determining the phase of each of the sub-wavefronts for use in interferometry.

3. Apparatus for sensing a wavefront including a reference wavefront and an object wavefront, the apparatus comprising:
   a wavefront-splitting element for splitting the wavefront into a plurality of sub-wavefronts;
   a phase-shifting interference element including a plurality of quadrants each for shifting the phase of a respective one of the sub-wavefronts by a multiple of 90° including 0°; and
   a sensing element including an active surface having a plurality of sections;
   wherein each of the sub-wavefronts follows an optical path from the wavefront-splitting element to a respective one of the quadrants of the phase-shifting element to a respective one of the sections of the active surface of the sensing element; and
   wherein each of the quadrants includes two plates such that each of the optical paths has a substantially equal path length.

4. The apparatus of claim 3 wherein at least one of the sub-wavefronts is incident on at least 80% of the surface area of a respective one of the sections of the active surface.

5. The apparatus of claim 4 wherein the phase-shifting interference element provides a plurality of phase-shifted interferograms, and wherein each of the phase-shifted interferograms is incident on substantially 100% of the surface area of a respective one of the sections.

6. The apparatus of claim 3 wherein at least one of the sub-wavefronts is adjacent to another one of the sub-wavefronts at the active surface.

7. The apparatus of claim 3 wherein the phase of each of the sub-wavefronts is measured simultaneously.

8. The apparatus of claim 3 further comprising a computer configured to provide data acquisition and processing, the computer being configured to receive data provided by the sensing element corresponding to the object wavefront acted upon by an object, the computer being configured to provide a measurement based on the data.

9. The apparatus of claim 8 wherein the measurement includes performing real-time interferometry on at least one transient event.

10. The apparatus of claim 8 wherein the measurement includes at least one of measuring a displacement of the object and measuring a three-dimensional profile of the object.

11. The apparatus of claim 8 wherein the object is one of a transparent solid, a transparent liquid, and a transparent gas, and wherein the measurement includes determining at least one of a pressure, a temperature, and a density gradient in the object.

12. The apparatus of claim 11 wherein the measurement of the displacement of the object includes at least one of the vibration and the strain of the object.

13. The apparatus of claim 8 wherein the object wavefront is acted upon by at least one of reflection and transmission.

14. The apparatus of claim 8 wherein the sensing element includes at least one charge coupled device (CCD).

15. The apparatus of claim 8 further comprising a laser in a transmit portion, the sensing element being included in an image portion and configured to provide imaging data, the computer being operatively connected to both the transmit and image portions to control the operation of the laser and to receive imaging data from the detector array.

16. The apparatus of claim 8, wherein the phase-shifting interference element provides a plurality of phase-shifted interferograms, and wherein the computer is configured to utilize a software program, the software program being configured to cause the computer to at least one of acquire, process, analyze, and display data associated with at least one phase-shifted interferogram.

17. The apparatus of claim 16 wherein acquisition includes two interferograms for each measurement.

18. The apparatus of claim 16 wherein a plurality of wrapped phase maps are determined for each of the interferograms and then subtracted from each other, the phase maps being unwrapped to provide a map of the phase change between the reference and object interferograms.

19. Apparatus for sensing a wavefront including a reference wavefront and an object wavefront, the apparatus comprising:
   a wavefront-splitting element for splitting the wavefront into a plurality of sub -wavefronts;
   a phase-shifting interference element including a plurality of quadrants each for shifting the phase of a respective one of the sub-wavefronts by a multiple of 90° including 0°; and
   a sensing element including an active surface having a plurality of sections;
   wherein each of the sub-wavefronts follows an optical path from the wavefront-splitting element to a respective one of the quadrants of the phase-shifting element to a respective one of the sections of the active surface of the sensing element; and
   wherein each of the quadrants is configured so that each of the optical paths has a substantially equal path length.

20. The apparatus of claim 19 wherein the phase-shifting interference element provides a plurality of phase-shifted interferograms, and wherein each of the phase-shifted interferograms is incident on substantially 100% of the surface area of a respective one of the sections.

* * * * *